United States Patent [19]
O'Brien et al.

[11] Patent Number: 4,726,672
[45] Date of Patent: Feb. 23, 1988

[54] ACUITY THERAPY UNIT
[75] Inventors: Richard W. O'Brien, Philadelphia; Gary Diamond, Bryn Mawr, both of Pa.
[73] Assignee: Visual Enhancement, Inc., Philadelphia, Pa.
[21] Appl. No.: 36,205
[22] Filed: Apr. 8, 1987

Related U.S. Application Data
[63] Continuation of Ser. No. 771,703, Sep. 3, 1985, abandoned.
[51] Int. Cl.⁴ ................................................ A61B 3/00
[52] U.S. Cl. .................................. 351/203; 351/222
[58] Field of Search ............... 351/203, 222, 223, 224, 351/226

[56] References Cited
U.S. PATENT DOCUMENTS

| | | |
|---|---|---|
| 3,421,498 | 1/1969 | Gans ...................................... 351/226 |
| 3,883,234 | 5/1975 | Lynn et al. |
| 4,239,351 | 12/1980 | Williams et al. |
| 4,294,522 | 10/1981 | Jacobs ................................... 351/203 |
| 4,353,626 | 10/1982 | Harrison |
| 4,408,846 | 10/1983 | Balliet |
| 4,533,221 | 8/1985 | Trachtman .......................... 351/203 |

Primary Examiner—John K. Corbin
Assistant Examiner—P. M. Dzierzynski
Attorney, Agent, or Firm—Ferrill and Logan

[57] ABSTRACT

An exercise device for improving poor visual acuity is disclosed in which a subject must identify randomly chosen figures of minimal visual stimulus projected in a darkened chamber. Earphones are provided to aid in the isolation of the subject and provide audio feedback. The device provides effective treatment for certain eye conditions involving poor acuity and is particularly effective in treating the eye condition known as amblyopia.

24 Claims, 3 Drawing Figures

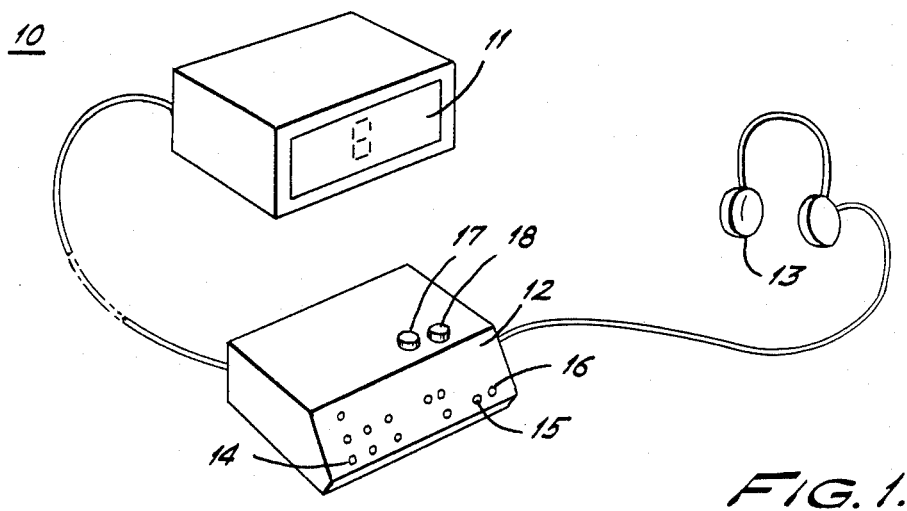
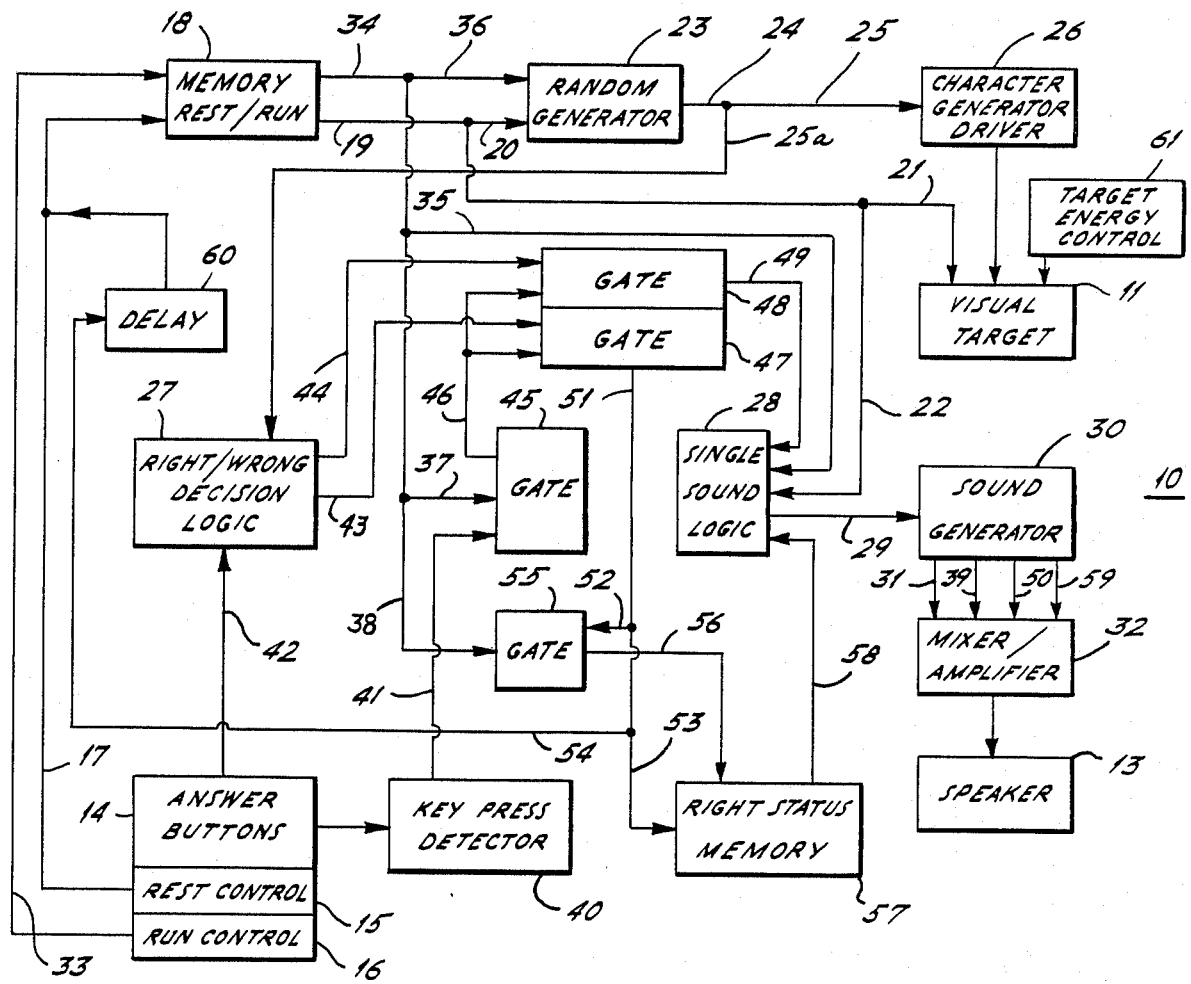
FIG. 1.
FIG. 2.

ACUITY THERAPY UNIT

This application is a continuation of application serial No. 771,703, filed Sept. 3 1985, now abandoned.

BACKGROUND OF THE INVENTION

The present invention relates to treatment of eye conditions caused by a loss of acuity where the origin of that loss is in the retina or brain and not of a refractive/transparent nature. Of particular concern is the treatment of the eye condition known as amblyopia.

Persons afflicted with amblyopia suffer from a mild to acute acuity loss in at least one of their eyes. This condition occurs despite a lack of evident structural change in the eye itself.

The only accepted treatment for amblyopia is the use of "patch therapy" during early childhood. This is usually attempted between the ages of a few months and about nine years.

Patch therapy involves covering the non-affected eye of the child and forcing the child to function using only the affected eye. However, if patch therapy provides no benefit by 9 years of age, the condition is deemed incurable.

Although patch therapy does have a good rate of success, it is far from a perfect method of treatment. First, it fails to cure every subject and thus leaves many children and adults without hope of treatment or improvement. Moreover, an unfortunate by-product of use of patch therapy for all subjects can be exposing the child to extreme frustration and danger. Many of these persons are legally blind in their affected eye (e.g. visual acuity of 20/200), and it is both cruel and unwise to force them to venture out into a highly visual world armed with little or no sight.

Concerned over the problems and shortcomings of patch therapy, the inventors embarked on an entirely different course of treatment. Attempting to stimulate the affected eye and its related portion of the brain, the inventors utilized absolute minimal stimulation. This is accomplished by visually and audibly isolating the subject. The theory is that the affected portion of the affected eye and its related portion of the brain must be coerced into functioning and this can only be accomplished by giving the person virtually nothing to observe except a small, barely visible and barely readable target. This treatment has proven effective, even on an adolescent subject who had previously been deemed incurable after 5 years of patch therapy that failed and was terminated at the age of 8.

In light of the foregoing, it is a primary object of the present invention to provide an apparatus for improving visual acuity by isolating the subject and producing minimal visual input.

It is a further object of the present invention to use the aforesaid apparatus as a therapeutic means for treating and curing amblyopia and render classic patch therapy obsolete for all subjects regardless of age.

Moreover, it is an object of the present invention to provide the therapeutic value of this invention in a simple, inexpensive and fully portable apparatus.

SUMMARY OF THE INVENTION

The present invention addresses the problem of how to effectively exercise eyes in order to improve extreme cases of poor acuity. Of particular concern is the eye condition of amblyopia. Employing a novel hypothesis of minimal optical stimulation, the present invention provides an ocular stimulator unit to be operated in a darkened room or chamber which includes: a lighted visual target or display, the apparent size of which is adjustable to a barely discernable size; electronic components which generate random letters or numbers on the visual display; a user keyboard; electronic components which compare the random figure displayed with responses from the user's keyboard and inform the user of the correctness of the response; and a pair of headphone speakers, which aid in the isolation of the subject and can provide audio feedback.

Utilizing the present invention provides effective and remarkable treatment of amblyopic subjects. The treatment is considerably safer and less burdensome than previously accepted methods of treating amblyopia (e.g. patch therapy), and has proven successful and is believed to be of great therapeutic value in improving subjects who were previously diagnosed as "incurable" using other methods.

The present invention is easy to use and does not require supervision. Moreover, its simplicity allows it to be reasonably priced and portable. The result is a superior therapeutic device which may be purchased by the average consumer and used in the home—where it can be of the maximum benefit.

DESCRIPTION OF THE DRAWINGS

The operation, features, and advantages of the present invention should become apparent from the following description when considered in conjunction with the accompanying drawings, in which:

FIG. 1 is a perspective view of one embodiment of the present invention;

FIG. 2 is a block diagram of the electronic components of the present invention.

DETAILED DESCRIPTION OF THE INVENTION

Figure 3:
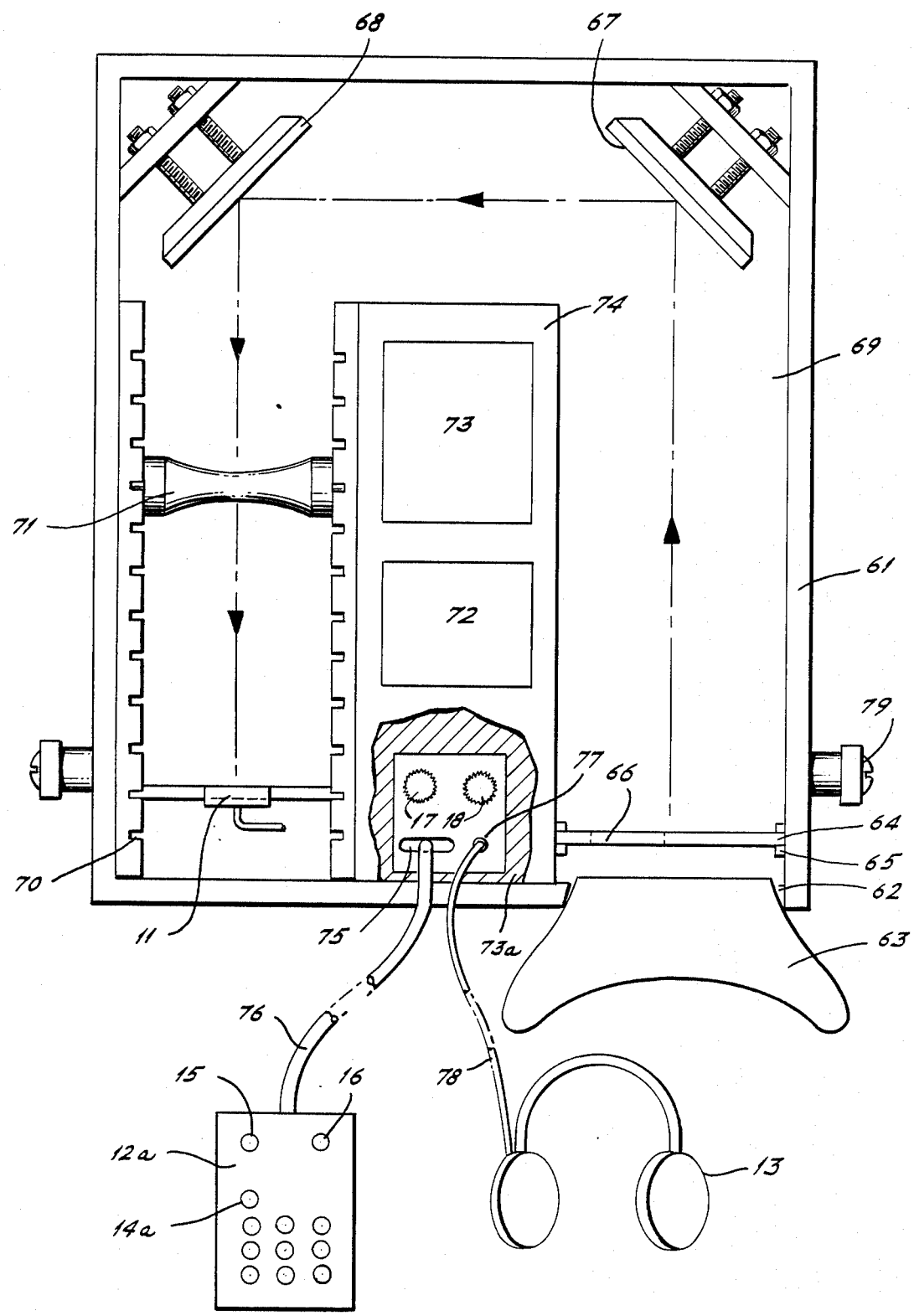
FIG. 3 is a top view of another embodiment of the present invention.

The present invention utilizes electronics to assist in the treatment and cure of certain eye conditions, particularly the eye condition known as amblyopia. The philosophy underlying the present invention is to place the subject in an environment of near complete sensory deprivation so to isolate the affected eye and encourage it, and that portion of the brain which receives sensory signals from it, to focus upon and identify a series of random figures or numbers of minimum size and discernibility. The subject must correctly identify the displayed item before the subject may continue on to the next figure or number.

There is illustrated in FIG. 1 an ocular stimulator unit 10. The unit 10 contains a visual target or display 11, a user keyboard 12, and a set of speakers or headphones 13. The unit 10 is operated in a substantially or completely darkened chamber, which may include a darkened room, an opaque hood, or an opaque box. The darkened chamber forces the subject to focus only upon the target 11.

It should be appreciated that consistent with the basic design philosophy, the present invention may be operated in a completely white room devoid of all shadows and other extraneous visual stimulus while using a dark target. However, it is doubtful that this environment will provide as fully an effective treatment as a darkened room.

The target 11 may be any type of known electronic display which may be viewed in the dark, including cathode ray tube, lighted liquid crystal display, or light emitting diode (L.E.D.) display. Additionally, lighted transparent or opaque photographic, printed, or photo engraved material may be used. In the preferred embodiment a seven segment L.E.D. display is utilized because of its low cost and superior edge sharpness with minimal extraneous sensory interference. It has been found that a display 11 which alternates between the displayed figure and its inverse (e.g. the inverse of "O" on a seven segment display is "-") or blinks on and off will retain the subject's attention for a longer period of time.

The speakers 13 provide both a "white noise" which aids in the isolation of the subject, and a series of audio signals which indicate the status of the unit 10 and the status of the subject's answers. Although any known speakers may be employed, headphones are preferred in that they create a more thorough isolation.

The keyboard 12 contains a series of answer buttons 14 which are arranged so that they may be distinguished upon touch alone. Additionally, a "rest" control 15 and a "run" control 16 are provided to allow the subject to command the rate and intensity of the treatment. It is also advisable to provide the subject with a volume control knob 17 to adjust the output of the speakers and a flicker control knob 18 to adjust the alternating or blinking rate of the display 11. The unit 10 can also be operated with the keyboard in control of an instructor who can record the oral responses of the subject. However, although an instructor may be necessary when utilizing the unit 10 with young or extremely "physically challenged" subjects, it is not preferred in that it detracts from the isolation of the subject and unduly limits the accessibility of treatment.

Referring to FIG. 2, operation of the present invention initiates in a "rest" status. Rest status occurs when the rest control button 15 is pressed. A signal from the rest control 15 enters the memory 18 via line 17. The memory 18 may comprise merely a flip flop circuit, such as a type 7476 flip flop. The memory 18 maintains the unit 10 in the rest status by producing a rest signal over output line 19. The rest signal over said line 19 feeds into three different lines 20, 21, and 22 to inputs of components 23, 11, and 28, respectively, which will be described below.

The signal fed through line 20 enters a random number generator 23. The random number generator 23 may comprise any known method of producing random numbers. In the preferred embodiment, the random number generator 23 comprises a gated clock and counter circuit set to produce a continuous series of numbers 0-9 at a high frequency. In the rest status, the random generator should "cycle thru" (i.e. continually producing the numbers). The random generator 23 produces a signal over line 24. In the rest status, said signal over line 24 will be constantly changing in accordance with the output of the random generator 23.

Line 24 feeds into two lines: line 25 conveying a character select signal, and line 25a conveying a current character signal. The character select signal conveyed by line 25 is converted by a character generator and display driver 26 of unique construction into a form which can be displayed on the visual target 11. The current character signal conveyed by line 25a is directed to a right/wrong decision logic circuit 27. The character generator and display drive 26 operates by phase shifting. A seven segment L.E.D. display 11 is driven by processing the character select signal 25 through a binary code decimal (b.c.d.) to 7 segment decoder, such as a type 7448 decoder. The decoder is only performing a decoder function and not the usual decoder-driver function. Each output of the decoder is attached to one input of seven exclusive OR gates, such as a type 7486 exclusive OR gate, and is used to reverse the phase shift of the gate. The seven gates are each used to drive each of the seven segments of the display. The flicker clock is fed to the remaining input of each of the seven gates. The display segments hence will flicker per the flicker clock except when the decoder induces a reverse in the phase shift of one or more exclusive OR gate. In this instance where the decoder reverses the phase of one or more exclusive OR gates, the phase of the clock drive to the corresponding segments of the display also will be shifted. In this fashion, information from the decoder will be projected on the display inverse to the remaining segments of the display in accordance to the flicker frequency of the flicker clock.

The signal conveyed by line 21 enters the visual target 11 and interrupts or "blanks" the display. This avoids producing confusing characters on the visual target 11 while the invention is in the rest status and produces a rest period for the subject.

The signal conveyed by line 22 enters a single sound logic 28, which will be described below. The sound logic 28 conveys a composite command signal via line 29 to a sound generator 30. The sound generator 30 may be a type 76477 sound generator chip. The sound generator 30 produces a rest sound signal via line 31 which passes to a mixer/amplifier 32. The mixer/amplifier 32 in turn alters the electrical impulses into a form which can be heard on the connected speakers 13.

In order to activate the present invention, the subject presses the run control button 16. The run control 16 produces a signal which enters the memory 18 via line 33. The memory 18 switches to and maintains a "run" status by producing a run signal over output line 34. The run signal over said line 34 feeds into four different lines 35, 36, 37, and 38 which respectively lead to inputs of the single sound logic 28, the random number generator 23, and components 45 and 55, which will be described below.

The signal conveyed by line 35 enters the single sound logic 28. The single sound logic 28 conveys composite signal via line 29 to the sound generator 30. The sound generator 30 produces a run sound signal via line 39 which is conveyed via the mixer/amplifier 32 to the speakers 13.

The signal conveyed by line 36 enters the random generator 23. The introduction of this signal interrupts the cycle of the random generator 23 at a random place in the cycle. The signal over line 24 and its resulting character select signal over line 25 and current character signal over line 25a will accordingly become fixed quantities.

The character select signal enters the character generator/display driver 26 via line 25 and is converted into a form which will be displayed on the visual target 11. The characters generated on the display 11 may be of any identifiable form, including alphanumeric figures. With the seven segment L.E.D. display, numbers 0 through 9 are preferred. The current character signal is directed to the right/wrong decision logic circuit 27 via line 25a.

At this juncture the subject may view the character on the target 11 and enter a response by pressing one of the answer buttons 14. The pressing of any answer button 14 activates a key press detector 40 which in turn produces a key press signal over line 41. Each answer button 14 is connected to the right/wrong decision logic 27 by line 42. The pressing of one of the answer buttons 14 produces an answer signal over line 42 to the right/wrong decision logic 27.

The right/wrong decision logic 27, which may be a type 7485 comparitor circuit, compares the current character signal 25a with the answer signal 42. If the two signals coincide, a right status signal is produced over line 43. If the two signals do not agree, a wrong status signal is produced over line 44.

The signal conveyed by line 37 and key press signals conveyed by line 41 enter a gate 45. The presence of both signals, signifying that the unit 10 is in the run status and that an answer key has been pressed, generates an enable signal over line 46. Line 46 feeds to the inputs of both gate 47 and gate 48.

The presence of both the wrong status signal conveyed by line 44 and the enable signal conveyed by line 46 at gate 48 generates a signal via line 49 to the single sound logic 28. An incorrect answer signal is produced by the sound logic 28 which enters the sound generator 30 via line 29. The sound generator 30 produces the incorrect answer sound signal 50 which is conveyed by line 50 through the mixer/amplifier 32 to the speakers 13. Upon receiving the audio response indicating an incorrect answer, the subject may then reexamine the visual target 11 and choose another possible answer.

Alternatively, the presence of both the right status signal over line 43 and the enable signal over line 46 at gate 47 generates a signal over line 51. The signal conveyed by line 51 feeds into three different lines 52, 53 and 54 which respectively lead to gate 55, and components 57 and 60, which will be described below.

The signal conveyed by line 52, signifying that a correct answer has been chosen, and the signal conveyed by line 38, signifying that the unit 10 is in the run status, both enter gate 55. When the signal conveyed by line 38 is present at gate 55 alone, a signal is produced over line 56 which passes to and clears a right status memory 57. As was true with memory 18, the right status memory 57 may be a flip flop circuit. When both the signal conveyed over line 38 and the signal conveyed over line 52 are present at gate 55, the signal conveyed over line 56 will cease and the right status memory 57 will no longer be maintained in the clear state. When the right status memory 57 receives the signal conveyed over line 53 without the interference of the signal conveyed over line 56, it produces and maintains a signal via line 58.

The signal conveyed by line 58 enters the single sound logic 28 and produces a correct answer signal which enters the sound generator 30 via line 29. The sound generator 30 produces the correct answer sound signal which is conveyed by line 59 via the mixer/amplifier 32 to the speakers 13. The signal conveyed by line 58 will continue until the unit 10 is reset in the run status which will produce the clearing signal via line 38.

The signal over line 54 passes through a delay 60 and becomes the signal entering memory 18 via line 17. This returns the unit 10 to the rest status until the run control button 16 is pressed again to repeat the run sequence.

The single sound logic 28 and the composite command signal produced over line 29 to the sound generator 30 operates in a known manner. The sound generator 30 is used to generate only two basic modes of sound: noise, and voltage controlled oscillator (vco) with super low frequency oscillator (slf).

Only the run sound induced by the signal conveyed by line 35 uses the noise mode. The incorrect answer sound, rest sound, and correct answer sound, induced by signals along lines 49, 22, and 58, respectively, all use the vco/slf mode.

The sound generator will remain in the noise mode unless it receives a signal via line 49, 22, or 58. The switch between noise mode and vco/slf is accomplished by a gate performing an OR function, such as a type 7420 NAND gate. The signals through lines 49, 22, and 58 enter the OR function gate which is set to respond if any of the three signals reverses logic state (e.g. goes low, if all three are high signals). The reversal of a logic state of the input to the OR function gate will change the output of the gate. The output of the OR function gate passes through an inverter, such as a type 7404 inverter, to the sound generator 30. The presence of a signal from the OR function gate at the sound generator 30 drives the sound generator 30 out of noise mode and into vco/slf mode. The putput from the inverter also functions to produce a vco/slf gain boost by using an open collector transistor function, such that which can be produced by a type 7407 buffer driver, to "pull down" a gain control resistor.

The signals conveyed by lines 49, 22, and 58 are also used to control the frequency of the vco and slf. Utilizing three buffer drivers, such as type 7407 buffer drivers, with three connected capacitors, each corresponding to one of the three lines, the three signals conveyed by lines 49, 22, 58 each enter the slf portion of the sound generator 30. Additionally, the signal via line 22 splits prior to entering its corresponding buffer driver and enters another buffer driver and capacitor. The output of the second buffer driver and capacitor of line 22 enters the vco portion of the sound generator 30. The desired sounds are chosen by selecting appropriate vco and slf capacitors.

Although any sound or no sound may be used in the operation of the present invention, it has been found that certain sounds are more conducive to the treatment process: the rest sound should be a soothing high to low to high "wave" sound; the run sound should be a static "white noise" which helps isolate the subject; the incorrect sound should be a "buzzer" noise; and the correct sound should be a trumpet, siren or other positive noise. It should be noted that effective treatments have also been accomplished utilizing various musical selections.

The figures displayed on the visual target 11 should be maintained at a minimum brightness at or near the subject's sensitivity threshold. To accomplish this, a target energy control 61 is employed. With a seven segment L.E.D. display the energy control 61 may comprise seven resistors which limit the energy each of the seven segments may receive. If it is desired, brightness of the entire display may be adjusted through use of optical neutral density filters.

To accomplish a treatment, the unit 10 and the subject are placed in a darkened room or chamber. The visual display 11 should be positioned far enough away from the subject that it can barely be read. It should be noted that the size of the target also can be adjusted by electrically altering the size of the figures. With the ear phones in place, the subject, using the answer buttons 14, attempts to identify each of the figures which appear on the visual display 11.

Although the unit 10 can be operated binocularly so to exercise both of the subject's eyes simultaneously, it is designed primarily to be operated monocularly, and particularly monocularly with amblyopic subjects. Persons suffering from the eye condition amblyopia usually have poor acuity in at least one of their eyes. To effect treatment of these subjects, the normal eye must be covered or otherwise isolated so that only the amblyopic eye can see the visual target 11. Naturally, the target should be positioned so that the affected eye is the one that can barely discern the figures. Additionally, the flicker or alternating rate of the target should be adjusted using the flicker control knob 18 so to make the target barely discernable.

Treatment of an amblyopic subject entails five minutes of identification of the displayed figures twice a day. Although to an extent the more time spent working with the unit 10 each day, the more effective is the strengthening of the eye, it must be appreciated that a major component of the present invention is dependant on a strong, positive mental attitude and a retraining of certain portions of the brain. Accordingly, all efforts should be made to make the treatments relatively short, enjoyable, and comfortable so to avoid mental fatigue.

It has been found that periodic treatments operating the unit at considerably greater than the subject's visual threshold may be necessary after treatments have been provided for an extended period of time so to avoid an observed relapse effect. It is believed that this is necessary to continue to selectively stimulate and train the entire fovea even though treatment has allowed the subject to identify smaller figures using a much narrower zone of the fovea.

FIG. 3 illustrates another embodiment of the present invention. In order to facilitate the frequent and easy use of the present invention, the unit 10 may be adapted to operate within a relatively small, self-contained carrying case 61.

In this embodiment, visual isolation is achieved by placing the visual target 11 inside opaque case 61 which when closed will not be susceptible to penetration by ambient light. The subject interfaces with the interior of the case 61 through an opening 62 in the side of the case 61. In order to avoid light seepage and increase the comfort for the subject, a shielding mask 63 made of soft rubber or other suitable material is provided.

In order to isolate only one eye for treatment, a slat 64 is provided which slides into slots 65 within the interior of the case 61. The slat 64 is provided with a hole 66 which permits only one of the subject's eyes a view of the interior of the case 61. The slat 64 may be reversed to switch eyes or it may be removed entirely so to operate binocularly.

Near focus orientation is not desirable. It is believed that the present invention is best operated in at least a medium focus zone with the virtual image of the target being 32 to 46 inches from the subject. In order to compact the unit, one or more mirrors 67, 68 are utilized to alter the path of light from the visual target 11 and the subject along a visual channel 69 in the interior of the case 61. In this manner the optical distance is increased without making the case 61 an unmanageable size.

A series of slots 70 are provided along the visual channel 69 which are adapted to receive the visual target 11. In this manner the distance, and thus the size, of the visual target 11 may be readily adjusted to account for varying degrees of acuity of the eye to be treated. Additionally, concave or convex lens 71 may be inserted in slots 70 in front of the target 11 so to further decrease or increase the size of the display 11.

The electrical components 72 and a power source 73 may be housed in storage space 74 located in the interior of the case 61 surrounded by the visual channel 69. The power source 73 may be either AC or DC current, but the transportability of the unit is greatly enhanced if batteries are employed.

The lid 73a of the case, shown in cut away, may contain a receptacle 75 for a cable 76 from the keyboard 12a, a receptacle 77 for the cable 78 from the headphones 13, the volume control knob 17, and the flicker control knob 18.

The handheld keyboard 12a, shown somewhat enlarged, contains the answer buttons 14a, the rest control button 15 and the run control button 16. In order to establish visual isolation, the various buttons on the handheld keyboard 12a must be discernable without need of examining the keys.

A movable handle 79 is attached to two sides of the case 61 towards the subject interface end. The handle 79 serves a dual role of both providing a means of easily carrying the case 61 and, when swung under the case 61 during use, as a stand to prop the unit into an inclined position for use.

The present invention provides a rigidly controlled environment of stimulation in contrast with the environment of chance stimulation present in classic patch therapy. Utilizing this new treatment apparatus in accordance with the above described method, acuity demand of stimulus is never permitted to become excessive and "crowding phenomenom," where the subject cannot distinguish between closely grouped figures, is totally absent. Hence the two probable causes of classic patch therapy failure are eliminated.

While particular embodiments of the present invention have been disclosed herein, it is not intended to limit the invention to such a disclosure, and changes and modifications may be incorporated and embodied within the scope of the following claims.

What is claimed is:

1. An ocular stimulator unit to improve the non-refractive acuity of a user's eyes comprising:
   a solitary visual target presented without interference from other visual stimulus;
   means for randomly selecting and generating at least one of a number of various figures to be displayed on said visual target;
   a keyboard through which the user can respond to the various figures seen on the visual target;
   means for comparing said displayed figure with responses from said keyboard;
   means for informing the user of the correctness or incorrectness of said response; and
   wherein means are provided for adjusting the apparent size of the displayed figure to maintain the figure displayed at a level of minimal discernable size.

2. Apparatus in accordance with claim 1 wherein means are provided to permit the user to control the rate of selection and generation of said random figures.

3. Apparatus in accordance with claim 2 wherein the means of controlling the rate of selection and generation of the random figures is a rest control and a run control.

4. Apparatus in accordance with claim 1 wherein said unit is operated in a darkened chamber.

5. Apparatus in accordance with claim 4 wherein the darkened chamber is an opaque box.

6. Apparatus in accordance with claim 1 wherein said visual target is capable of being viewed in the dark.

7. Apparatus in accordance with claim 6 wherein said visual target is chosen from the group of cathode ray tube displays, lighted liquid crystal displays, light emitting diode displays, and lighted transparent or opaque materials.

8. Apparatus in accordance with claim 7 wherein said visual target is a light emitting diode display.

9. Apparatus in accordance with claim 1 wherein said means for adjusting the apparent size of the displayed figure comprises means for changing the visual distance between the user and the displayed figure.

10. Apparatus in accordance with claim 9 wherein the visual distance is changed by using one or more mirrors.

11. Apparatus in accordance with claim 1 wherein said means for adjusting the apparent size of the displayed figure comprises using one or more lenses.

12. Apparatus in accordance with claim 1 wherein the apparent size of the displayed figure is adjusted by changing the size of characters displayed by the displayed figure.

13. Apparatus in accordance with claim 1 wherein the keyboard contains a series of buttons each corresponding to one of the figures to be generated and displayed.

14. Apparatus in accordance with claim 1 wherein the random figures are selected and generated using a random generator, a character generator, and a display driver.

15. Apparatus in accordance with claim 14 wherein the random generator is a gated clock and counter circuit.

16. Apparatus in accordance with claim 1 wherein the means for comparing the displayed figure with the user's response is a right/wrong decision logic circuit.

17. Apparatus in accordance with claim 1 wherein audio feedback is provided to the user informing the user of the status of the responses and the unit.

18. Apparatus in accordance with claim 17 wherein said audio feedback is provided to the user through earphone speakers.

19. Apparatus in accordance with claim 1 wherein means are provided to cover one of the user's eyes during operation of the unit.

20. A method for use in improving the non-refractive acuity of a user's eye, said method comprising;
placing before the user's eye a solitary visual target presented without interference from other visual stimulus;
causing the visual target to randomly display at least one of a number of predetermined characters;
providing the user with keyboard means capable of being so actuated by the user as to denote any of said characters the user believes he or she discerns upon the visual target;
comparing the character denoted through the keyboard with the displayed character to detect and signify whether they coincide with each other; and
providing means for adjusting the apparent size of said displayed character to maintain the character displayed at a level of minimal discernable size.

21. The method as defined in claim 20, wherein the visual target provides a luminous image, and said method is practice in a condition of substantial darkness.

22. The method as defined in claim 20, further including the step of adjusting at least one of the following prevailing conditions so as to maintain substantially threshold visibility and discernability of the randomly presented characters: the optical distance between the user's eye and the visual target, the ambient light level, the intensity of character illumination of the display target, and the apparent size of the characters.

23. The method as defined in claim 20, further including the steps of introducing a flicker-like effect in the image presentation.

24. Apparatus in accordance with claim 1 wherein means are provided to adjust the discernability of said figures through phase shifting of said visual target, and wherein said means includes providing a visual target which comprises: a character generator, a display driver and a multiple segment L.E.D. display, phase shifting of segments of said display provided through;
a flicker clock with an adjustable clock frequency control;
a decoder; and
multiple exclusive-OR gates each electrically connected between said flicker clock and said decoder, and one segment of said display.

* * * * *